US00PP14590P29

(12) United States Plant Patent
Hanes

(10) Patent No.: US PP14,590 P2
(45) Date of Patent: Mar. 9, 2004

(54) VERBENA PLANT NAMED 'LAN LAV STAR'

(50) Latin Name: *Verbena hybrida*
Varietal Denomination: Lan Lav Star

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 21 days.

(21) Appl. No.: 10/389,076

(22) Filed: Mar. 13, 2003

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Susan B. McCormick
(74) *Attorney, Agent, or Firm*—Jondle & Associates, PC

(57) ABSTRACT

A verbena cultivar particularly distinguished by purple colored flowers, vigorous growth.

1 Drawing Sheet

Genus and species: Verbena hybrida.
Variety denomination: 'Lan Lav Star'.

BACKGROUND OF THE NEW PLANT

The present invention comprises a new and distinct cultivar of verbena, botanically known as Verbena hybrida, and hereinafter referred to by the cultivar name 'Lan Lav Star'. The new cultivar is asexually reproduced from vegetative cuttings and tissue culture resulting from the cross of the seed/pod parent Temari Purple, a commercial line that is unpatented × 99-765-5 a pink with blue tones proprietary line that is unnamed and unpatented. This seedling had a purple with a small white eye flower. The instant plant is the result of a Sport from this cross.

'Lan Lav Star' is a product of a planned breeding program intended to create new verbena cultivars with purple colored flowers, dark green foliage, vigorous growth.

The new cultivar was created in 1999 in Gilroy, Calif. and has been asexually reproduced repeatedly by vegetative cuttings and tissue culture in Gilroy, Calif., Andijk, The Netherlands; Guatemala over a three year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Lan Lav Star'. The data, which defines these characteristics, were collected from asexual reproductions carried out in Gilroy, Calif. The plant history was taken on 6 month old plants grown in one-gallon pots, in a double poly-greenhouse under natural light and color readings were taken in the greenhouse under natural lights. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Verbena hybrida.
*Commercial.*—Verbena.
Form: Semi upright and spreading.
Growth and branching habit: Vigorous growing, moderate basal branching.
Height: From soil level to top of blooms: Approximately 20–25 cm.
Width: Approximately 20–30 cm.
Time to produce a finished flowering plant: 11 weeks.
Outdoor plant performance: Typical bedding plant culture, full sun in the garden, hanging baskets or container plants.
Time to initiate and developed roots: Approximately 4–10 days in the greenhouse.
Root description: Fibrous, fleshy, white.

THE LEAVES

Leaf arrangement: Opposite.
Length: 5.2–5.9 cm.
Width: 3.3–3.7 cm.
Leaf blade shape: Ovate.
Leaf margin: Pinnatified, irregularly incised.
Apex aspect: Obtuse.
Base aspect: Acuminate.
Leaf color: Upper side — Between RHS 139A (green) and 147A (yellows-green); Underside — Closest to RHS 147B (yellow-green).
Texture: Hirsute and some glandular hairs with violet hue.
Venation: Palmate.
Venation color: RHS 144B (yellow-green) fading from base until almost disappears into leaf.
Petiole length: 1.0–1.2 cm.
Petiole diameter: 0.2–0.3 cm.
Petiole color: RHS 144B (yellow-green).

Petiole texture: Hirsute and some glandular hairs with violet hue.

THE STEM

Length: 30–40 cm.
Diameter: 0.25–0.3 cm.
Internodes length: 2.0–3.5 cm.
Color: RHS 144A (yellow-green) but a little darker.
Texture: Hirsute of long and short sizes and glandular hairs with violet hue.
Stem anthocyanin: No.

THE BUD

Shape: Linear.
Diameter: 0.3 cm.
Length: 1.4–1.9 cm.
Color at tight bud: RHS N82D BC (purple-violet) with RHS 85D (violet) patches.

THE FLOWER

Blooming habit: Flowers continuous throughout the growing season, early blooming, center flowering in the plant.
Inflorescence type: Spike.
Spike diameter: 5.0–5.5 cm.
Spike depth: 3.0–3.4 cm.
Peduncle length: 3.5–6.0 cm.
Peduncle diameter: 0.2 cm.
Peduncle color: RHS 144A (yellow-green).
Peduncle texture: Hirsute and many glandular hairs of various sizes with dark violet hue.
Flower color: Front side, RHS 84A (violet) but a little lighter base color; RHS 76C (purple) linear patches on each side of the petals, approximately 1.5 cm wide.
Flower color: Underside, RHS 84C (violet) but lighter base color; RHS 76D (purple) linear patches on each side of the petals approximately 1.5 cm wide.
Color of throat hairs: RHS 150A (yellow-green).
Floret form: Salverform; sessile on spikes.
Floret (limb) diameter: 1.7–2.0 cm.
Corolla tube length: 2.0–2.5 cm.
Number florets per spike: 19–28.
Number of petals: Gamopetalous, five lobed.
Petal size: Length of one lobe — 0.8–0.9 cm. Width of one lobe — 0.7–0.9 cm.
Petal lobe shape: Obovate.
Petal apex shape: Emarginate.
Petal base shape: Fused.
Petal margin: Entire.
Petal texture: Papillose.
Sepals: Five sepals whose margins are fused to each other along their length with a transparent membrane of less than 1 mm in width with one smaller sepal attached to the base of the calyx.
Calyx length: 1.2–1.3 cm.
Calyx width: 0.25–0.3 cm.
Calyx shape: Linear.
Calyx apex: Acute.
Calyx color: Between RHS 143A and B (green).
Calyx texture: Hirsute and many glandular hairs in light and dark violet hues.
Lastingness of individual blooms: 1 week.
Fragrance: None.

THE REPRODUCTIVE ORGANS

Not conspicuous: Usually 4 stamens, in 2 pairs; 1 pistil; typical of Verbena.
Seed production: Not observed.

DISEASE AND INSECT RESISTANCE

Mildew tolerance.

COMPARISON WITH KNOWN CULTIVARS

'Lan Lav Star' differs in the following ways. 'Lan Lav Star' is a bicolor flowered while the parent has a purple with a small eye flower.

I claim:

1. A new and distinct cultivar of verbena plant as shown and described herein.

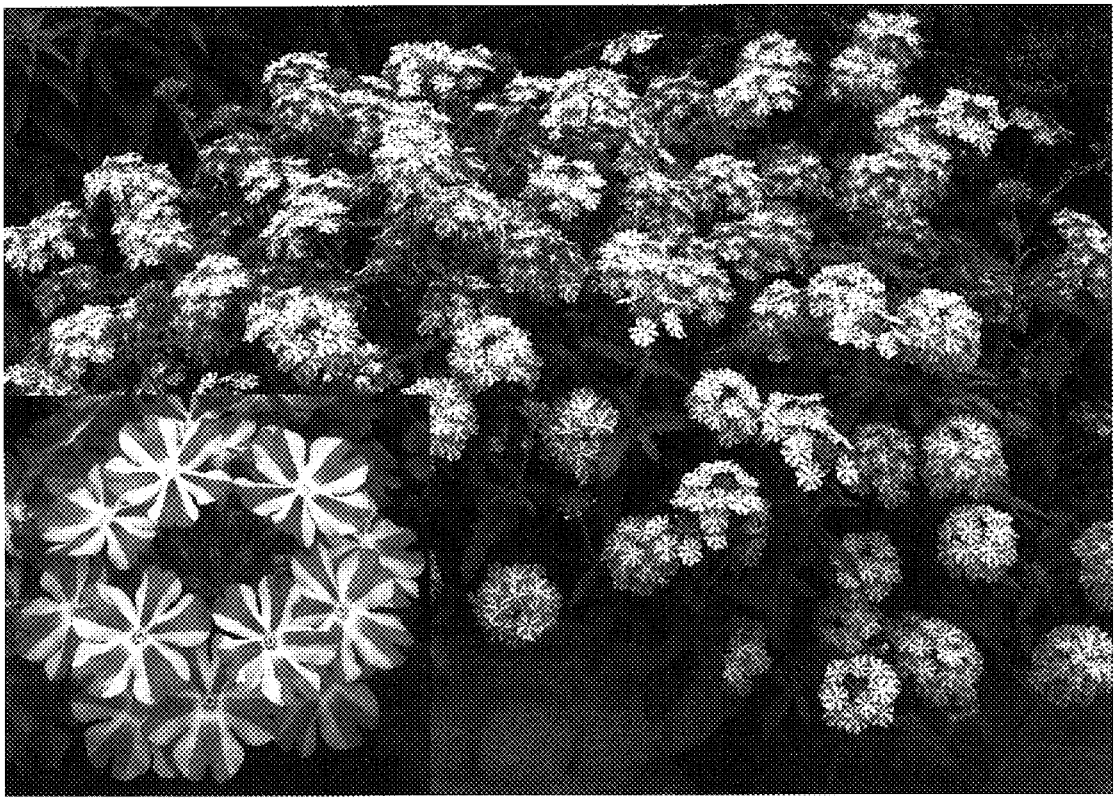

* * * * *